United States Patent [19]

Ambrosi et al.

[11] Patent Number: 4,556,414

[45] Date of Patent: Dec. 3, 1985

[54] HERBICIDAL DIHYDROPYRIDINE AMIDES

[75] Inventors: Dominique Ambrosi, Charbonniers-les-Bains; de Reinach Hirtzbach François, Lyons, both of France

[73] Assignee: Rhone-Poulenc Agrochimie, Lyon, France

[21] Appl. No.: 391,439

[22] Filed: Jun. 23, 1982

[30] Foreign Application Priority Data

Jun. 25, 1981 [FR] France ................. 81 12698

[51] Int. Cl.$^4$ ............... A01N 43/40; C07D 211/90
[52] U.S. Cl. ....................... 71/94; 546/316; 546/286; 546/287; 546/291; 546/296; 546/298; 546/299; 546/300; 546/301; 546/302; 546/270
[58] Field of Search ............ 546/316, 286, 287, 291, 546/296, 298, 299, 300, 301, 302, 270; 71/94

[56] References Cited

U.S. PATENT DOCUMENTS

| | | |
|---|---|---|
| 4,031,104 | 6/1977 | Bossert et al. ............ 546/321 |
| 4,201,715 | 11/1978 | Deinhammer et al. ............ 546/316 |
| 4,256,749 | 3/1981 | Horstmann et al. ............ 546/321 |

FOREIGN PATENT DOCUMENTS

| | | |
|---|---|---|
| 3105 | 1/1979 | European Pat. Off. . |
| 44262 | 7/1981 | European Pat. Off. . |
| 998225 | 10/1949 | France . |
| 2248028 | 5/1975 | France . |
| 2381029 | 9/1978 | France . |
| 2387960 | 11/1978 | France . |
| 140463 | 11/1975 | Japan . |
| 5233676 | 3/1977 | Japan . |
| 1426499 | 2/1976 | United Kingdom . |
| 1573576 | 12/1977 | United Kingdom . |

OTHER PUBLICATIONS

Streitwieser et al. "Introduction to Organic Chemistry", 1976, pp. 569–570.

A. R. Katrintzky et al., *The Principles of Heterocyclic Chemistry,* p. 20 (1968).
Klingsberg, *Pyridine and Its Derivatives,* Part 1, p. 80.
W. Theilheimer, *Synthetic Methods of Organic Chemistry,* vol. 13, p. 352.

*Primary Examiner*—Henry R. Jiles
*Assistant Examiner*—Dale A. Bjorkman
*Attorney, Agent, or Firm*—Burns, Doane, Swecker & Mathis

[57] ABSTRACT

Selective herbicides based on compounds of the formula:

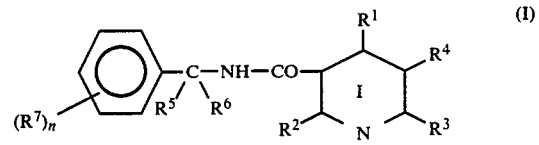

in which:
R$^1$, R$^2$ and R$^3$ are H, lower alkyl, alkoxy or alkoxyalkyl;
R$^4$ is a carboxyl radical, optionally in the form of a salt or ester, or a cyano, cyanoalkyl or alkoxyalkyl radical;
R$^5$ and R$^6$ are H, lower alkyl or cyano or together form a C$_2$ to C$_5$ alkylene radical;
R$^7$ is halogen, lower alkyl, lower alkoxy, lower alkenyl, alkenyloxy, nitro, cyano or amino, alkylenedioxy;
n=0 to 5; and

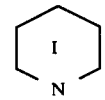

is a nitrogen-containing heterocyclic ring containing 2 or 3 units of unsaturation.

10 Claims, No Drawings

HERBICIDAL DIHYDROPYRIDINE AMIDES

The present invention relates to new compounds containing an amide group, derived from pyridine, and to the process for their preparation, the herbicidal compositions in which they are present and their application for selectively destroying weeds in crops, in particular cotton and sunflower.

Pyridine derivatives containing an amide group, and more particularly the dianilide derivative of 3,5-dicarboxy-2,6-dimethylpyridine, have already been proposed (European Pat. No. 3,105) as plant-protection agents. However, such compounds are not satisfactory as herbicides. Dihydropyridine derivatives containing an amide or ester group have also been described (French Pat. No. 988,225), but these products are simply known as agents for bleaching textile articles.

The object of the invention is to provide new selective herbicides of the family of the pyridine derivatives.

It has now been found that this object can be achieved by virtue of the new derivatives according to the invention.

These derivatives are products of the formula:

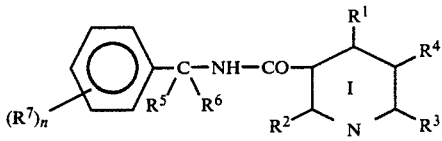 (I)

in which:
- $R^1$, $R^2$ and $R_3$, which are identical or different, represent the hydrogen atom, a lower alkyl radical, a lower alkoxy radical or an alkoxyalkyl radical having from 2 to 8 carbon atoms;
- $R^4$ represents an organic radical, such as the carboxyl radical, optionally in the form of a salt or ester, or the cyano radical, a lower cyanoalkyl radical or an alkoxyalkyl radical having from 2 to 8 carbon atoms;
- $R^5$ and $R^6$ represent the hydrogen atom or a lower alkyl radical or together form a single divalent alkylene radical having from 2 to 5 carbon atoms, it also being possible for one of these radicals $R^5$ and $R^6$ to represent a cyano radical;
- $R^7$ represents a halogen atom, a lower alkyl radical, a lower alkoxy radical, a lower alkenyl radical, a lower alkenyloxy radical (these various alkyl, alkoxy, alkenyl and alkenyloxy radicals being optionally halogen-substituted), a nitro or cyano radical or an optionally substituted amino radical; or, when several $R^7$ are present, two of them may together represent an alkylene-dioxy group having from 1 to 4 carbon atoms;
- n is zero or a positive integer equal to at most 5 (n=0 to 5); if n is greater than 1, the various substituents $R^7$ can be identical or different; and
the heterocyclic ring

represents a 6-membered unsaturated nitrogen-containing heterocyclic ring which can contain 2 or 3 units of unsaturation or double bonds.

In the present account, unless especially indicated otherwise, the adjective "lower", qualifying an organic radical, means that this radical contains at most six carbon atoms ($C_1$–$C_6$).

More specifically, the unsaturated nitrogen-containing heterocyclic ring

can represent either a pyridine nucleus or a dihydropyridine nucleus.

If this unsaturated nitrogen-containing heterocyclic ring represents a dihydropyridine nucleus, the products according to the invention then have the formula:

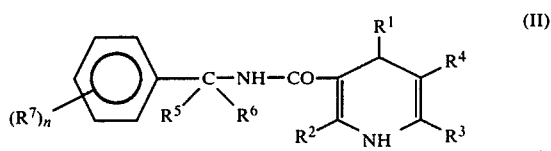 (II)

in which the various symbols $R^1$ to $R^7$ and n have the meanings given above.

If the unsaturated nitrogen-containing heterocyclic ring

represents a pyridine nucleus, the products according to the invention then have the formula:

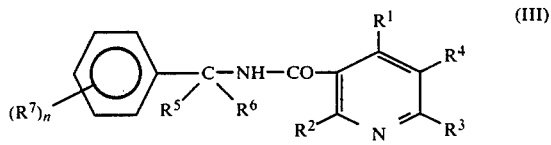 (III)

in which the various symbols $R^1$ to $R^7$ and n have the meanings given above.

The invention obviously relates also to the possible tautomeric forms of the products of the formula (I).

Advantageously, if the compound according to the invention is in the form of a salt or ester, the radical $R^4$ is chosen from amongst the following radicals:
salified COOH radicals constituting an agriculturally acceptable salt; this COOH radical can be salified by an inorganic base (e.g. sodium hydroxide or potassium hydroxide) or an organic base (e.g. a primary, secondary or tertiary amine, in particular mono-, di- or trialkylamines); and
the radical —COOR$^8$, R$^8$ being a lower alkyl radical.

Also advantageously, if the radical $R^7$ represents a substituted amino radical, it can be substituted by one or two (identical or different) lower alkyl radicals or by a radical —CO—R$^9$, in which R$^9$ represents a lower alkyl, lower alkoxy, lower alkylamino or dialkylamino radical, in which each of the alkyl parts, which are identical or different, contains at most 6 carbon atoms.

Some of the various products of the formula (I) constitute a preferred class; these are the products in which:
$R^1$ is the hydrogen atom;
$R^2$ and $R^3$ are independently and methyl radical, the methoxy radical or a lower alkoxyalkyl radical;
$R^4$ is $COOR^8$, $R^8$ having from 1 to 4 carbon atoms (e.g. the methyl and ethyl radicals, in which case $R^4$ is a methyl or ethyl carboxylate), a lower cyanoalkyl radical or a lower alkoxyalkyl radical;
$R^5$ and $R^6$ are the hydrogen atom or one of them is the methyl radical, or they together form an alkylene chain having from 2 to 3 carbon atoms;
$R^7$ is a halogen atom (in particular a chlorine or fluorine atom), an alkyl radical having from 1 to 4 carbon atoms (e.g. methyl or ethyl), which is optionally halogen-substituted (e.g. trifluoromethyl), or an alkoxy radical having from 1 to 4 carbon atoms; and
n is equal to 0, 1 or 2.

Depending on the nature of the substituents, the compounds of the formula (I) can be in the racemic form or in the form of optical antipodes. In particular, if $R^5$ and $R^6$ are different, two forms of optical isomers exist, which also form part of the invention. The optical isomers having the same optical configuration as (1)-α-methylbenzylamine are advantageous.

The compounds of the formula (II) according to the invention can be prepared by a process which also forms part of the invention. This process consists in reacting an aldehyde of the formula $R^1$—CHO with an aminoethylene derivative of the formula (IV) and with a ketoamide of the formula (V):

(IV)

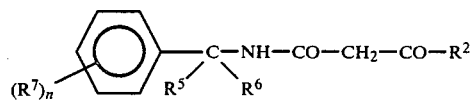

(V)

in which formulae $R^1$, $R^2$, $R^3$, $R^4$, $R^5$, $R^6$, $R^7$ and n have the meanings given above.

The reaction is carried out in accordance with the following equation:

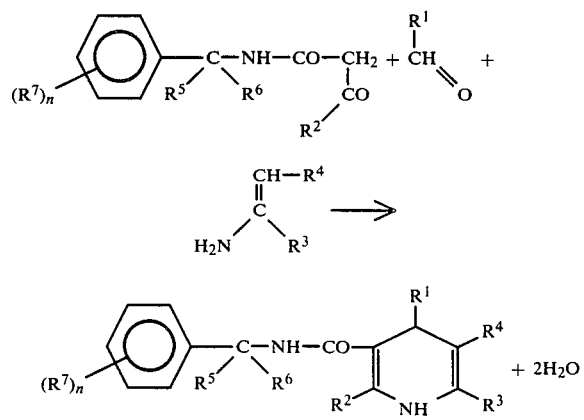

The reaction temperature is generally between +10° C. and the degradation temperature of the reactants and/or reaction products. Temperatures between 15° and 100° C. are generally suitable. As the reaction is exothermic, it can initially be carried out at ambient temperature, the temperature rising by itself during the reaction; it is also possible to carry out the reaction at the b.p. of the reaction medium (reflux temperature of the solvent if one is used).

The reaction of the process according to the invention for the preparation of products of the formula (II) is advantageously carried out in the presence of an inert organic solvent, i.e. an organic solvent which does not react chemically with the reactants and/or reaction products.

As suitable solvents, there may be mentioned customary protic or aprotic organic solvents, such as aromatic hydrocarbons, in particular benzene, toluene and xylenes; aliphatic or cycloaliphatic hydrocarbons, in particular octane, decane, dodecane, cyclohexane and methylcyclohexane; halogenohydrocarbons, in particular 1,2-dichloroethane, chloroform and carbon tetrachloride; lower alkanols, in particular methanol. ethanol, isopropanol and tert.-butyl alcohol; ethers, in particular ethyl ether; nitriles, in particular acetonitrile; amides, in particular dimethylformamide; and ketones, in particular acetone and methyl isobutyl ketone.

The reaction of the process according to the invention for the preparation of products of the formula (II) is most conveniently carried out by simply bringing the various reactants into contact, in the presence of the solvent. Advantageously, it is preferred to dissolve the ketoamide of the formula (V) and the aminoethylene derivative of the formula (IV) in the chosen solvent, and the aldehyde $R^1CHO$ is then reacted with the solution thus obtained.

The various reactants are preferably used in stoichiometric amounts; it is also possible to use amounts which differ by up to 10 mol %, and even 30 mol %, from stoichiometry.

The concentration of reactants in the reaction medium is usually more than 5% by weight and less than the solubility limit of the reactants; concentrations of 10 to 40% by weight are generally suitable.

At the end of the reaction, the product of the formula (II) is separated from the reaction mixture by the customary techniques, most frequently by simple crystallisation on cooling.

The optical isomers of the products according to the invention can be prepared by any process which is in itself known. One process consists in separating the optical antipodes from racemic mixtures. A more convenient process consists in simply using, as the reactant, an optically active ketoamide of the formula (V), itself derived from an optically active amine of the formula:

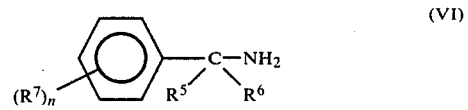

(VI)

The reaction of the process of the invention for the preparation of products of the formula (II) is not accompanied by optical inversion, so that it is advantageous to choose amines of the formula (VI) having the same configuration as that of the desired product.

In general, the aldehyde $R^1CHO$ and the reactant of the formula (IV) are well-known products or even commercial products. The ketoamide of the formula (V) can be prepared e.g. by a process such as that described in "Organic Syntheses, Collective Volume 3, page 10", using the appropriate starting materials.

The compounds of the formula (III) according to the invention can be prepared by a process which also forms part of the invention.

This process comprises dehydrogenating a dihydropyridine of the formula (II).

This dehydrogenation can be carried out by methods which are in themselves known and which are described, in particular, in Chemical Reviews 1972, Volume 72, No. 1, page 31, such as:

reaction with an oxidising agent, such as nitric acid, nitrous acid (generally formed in situ by reacting sodium nitrite with acetic acid), chromic acid, iodine, sulphur or potassium permanganate; or heating of the dihydropyridine of the formula (II), optionally in the presence of a dehydrogenation catalyst, such as e.g. palladium.

In the case of some of the compounds prepared, it has furthermore been observed that the dehydrogenation of the dihydropyridine to give the corresponding pyridine sometimes takes place spontaneously, in the open air or under an oxygen-containing atmosphere, at or above ambient temperature, without using a catalyst, after a longer or shorter time (e.g. during dissolution in acetic acid at between 20° and 50° C.).

Advantageously, the conversion of the dihydropyridine of the formula (II) to the pyridine of the formula (III) is carried out by reacting sodium nitrite with a suspension of the dihydropyridine of the formula (II) in acetic acid. As the reaction is exothermic, it is generally preferred to cool the reaction mixture so that its temperature does not exceed 25° C.

The preparation of products of the formula (III) from products of the formula (II) is also not accompanied by optical inversion, so that the products of the formula (II) and the products of the formula (III) derived therefrom have the same optical configuration.

The compounds corresponding to the formula (III) in which $R^4$ represents a cyanoalkyl radical, it being possible for the other substituents to have the same meanings as in the formula (III), can be prepared by reacting sodium cyanide with a chloroalkylpyridine of the formula (VI):

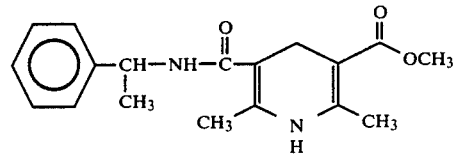

in which m is equal to a number from 1 to 4.

The reaction is advantageously carried out in an aqueous medium at ordinary temperature.

The compounds corresponding to the formula (III) in which $R^4$ represents an alkoxyalkyl radical, it being possible for the other substituents to have the same meanings as in the formula (III), can be prepared by reacting an appropriate alkali metal alkanolate with the chloroalkylpyridine of the formula (VI).

This reaction is advantageously carried out in an anhydrous alkanol, e.g. methanol, by means of sodium.

The compound (VI) can be prepared from a compound corresponding to the formula (III) in which $R^4$ is a methoxycarbonyl radical, this methoxycarbonyl group being converted to a hydroxyalkyl group (e.g. by reduction by means of lithium aluminium hydride), and this hydroxyalkyl group then being converted to a chloroalkyl group by reaction with a halogenating agent, such as e.g. $SOCl_2$.

Analogously, compounds corresponding to the formula (II) in which $R^4$ represents a cyanoalkyl or alkoxyalkyl radical can be prepared from compounds of the formula (II) in which $R^4$ represents the methoxycarbonyl radical.

The examples below, which are given without implying a limitation, illustrate the invention and show how it can be put into practice.

The structure of the compounds was confirmed by infra-red spectrometry and/or by nuclear magnetic resonance spectrometry (NMR); the NMR spectra were run at 60 megahertz in dimethylformamide, with hexamethyldisiloxane as the standard.

Examples 1 to 7 illustrate the preparation of the compounds according to the invention.

In these examples, $[\alpha]_D^{20}$ denotes the optical rotation at 20° C. for the sodium D line, the measurement being carried out in dimethylformamide.

Examples 8 to 10 illustrate the herbicidal compositions in which the compounds according to the invention are used, together with the application of these compositions.

Tables (I) to (V) give the nature and the physical properties of the compounds prepared; Tables (VI) to (XII) illustrate the herbicidal application of these compounds.

EXAMPLE 1

Preparation of (d)-1,4-dihydro-3-N-(α-methylbenzyl)-carbamoyl-5-methoxycarbonyl-2,6-lutidine (dextrorotatory Compound No. 21) of the formula:

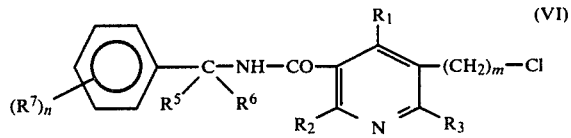

The following are introduced into a 1 liter three-necked round-bottomed flask equipped with a condenser, a thermometer and a central mechanical stirrer:

(1)-N-(α-methylbenzyl)-acetoacetamide (112 g; 0.546 mol), methyl β-aminocrotonate (69 g; 0.6 mol) and ethanol (110 ml).

The mixture is stirred at ambient temperature and then heated to 35° C. When the reactants have dissolved, a 30% strength by weight aqueous solution of formaldehyde (60 ml; i.e. about 0.6 mol) is run into the mixture. The reaction is exothermic and the temperature rises spontaneously to 75° C. The reaction mixture is then heated under reflux for 60 minutes.

After cooling, the precipitate is filtered off. This gives a mixture containing the desired product and also, as a by-product, 1,4-dihydro-3,5-dimethoxycarbonyl-2,6-lutidine, the formation of which results from the condensation of 2 mols of methyl β-aminocrotonate with one mol of formaldehyde.

The expected product (22 g) is obtained by recrystallisation from ethanol (5 ml/g).

Yield relative to the starting (1)-N-(α-methylbenzyl)-acetoacetamide: 13%

M.p: 180° C.
Empirical formula: $C_{18}H_{22}N_2O_3$
$[\alpha]^{20}$: 128° C.

The starting (l)-N-(α-methylbenzyl)-acetoacetamide was prepared by reacting (l)-α-methylbenzylamine with diketen by the method described in "Organic Syntheses, Collective Volume 3, page 10" for the preparation of acetoacetanilide.

EXAMPLE 2

Preparation of Compounds 1 to 31

Compounds Nos. 1 to 31 were prepared by following the procedure described in Example 1, using the appropriate starting materials. The formulae, the m.p. and the yield obtained in the course of the preparation are indicated in Tables (I), (II) and (III).

The products of Table (I), and also Compound 31 of Table (III), cannot give rise to optical isomerism. Compounds Nos. 20 and 24 to 30 are racemates, as is the amine used as the starting reactant. Compound 21 is optically active, as already described in Example 1. Compound 22 is optically active, having been prepared from a starting amine in the form of a pure laevorotatory optical isomer. Compound No. 23 is optically active, having been prepared from a starting amine in the form of a pure dextrorotatory optical isomer.

EXAMPLE 3

Preparation of (d)-3-methoxycarbonyl-5-[N-(α-methylbenzyl)-carbamoyl]-2,6-lutidine (Compound No. 70) of the formula:

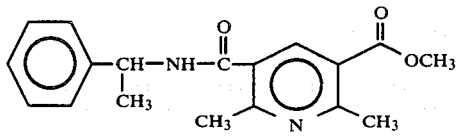

The following are introduced into a 250 ml three-necked round-bottomed flask equipped with a condenser, a thermometer and a central mechanical stirrer:

(d)-1,4-dihydro-3-methoxycarbonyl-5-[N-(α-methylbenzyl)-carbamoyl]2,6-lutidine (Compound No. 21) (5 g; 0.015 mol) and
acetic acid (40 ml).

The reaction mixture is cooled to 16° C. and sodium nitrite (1.1 g; 0.015 mol) is added in small portions.

The exothermic reaction is controlled by cooling with the aid of an ice bath so that the temperature of the reaction mixture does not exceed 25° C.

After stirring for 30 minutes at about 20°-25° C., the mixture is poured onto ice and neutralised with concentrated ammonia solution (50 ml). Extraction is carried out with methylene chloride (2×100 ml). After drying over sodium sulphate and evaporation of the organic phase, a crude product (5 g) is obtained. It is filtered on silica (150 g), elution being carried out with a mixture of methylene chloride and acetone in respective proportions by volume of 85/15. This yields a product (3.2 g), which crystallises spontaneously. It is washed with ether and the desired compound (2.3 g) is obtained in the form of a white powder.

M.p: 129° C.
Yield (from the dihydrolutidine): 46%
Empirical formula: $C_{18}H_{20}N_2O_3$
$[\alpha]^{20}$ = +30°

EXAMPLE 4

Compounds Nos. 51 to 87 were prepared by following the procedure described in Example 3, using the appropriate starting materials. The formulae, the m.p. and the yield obtained in the course of the preparation are indicated in Tables (IV) and (V).

The products of Tables (IV) and (V) in which the radicals $R^5$ and $R^6$ are identical cannot give rise to optical isomerism; in the case of the other products, the amine starting reactant and also the compounds obtained were all racemic, except for Compounds 59, 60 and 70, which are optical isomers, as is the amine starting reactant, which was dextrorotatory, laevorotatory and laevorotatory for these three compounds respectively. The optical rotation $[\alpha]^{20}$ of Compounds 59, 60 and 70 is respectively −16°, +18° and +30°.

EXAMPLE 5

Preparation of 2-methyl-3-[N-(α-methylbenzyl)-carbamoyl]-5-ethoxycarbonyl-6-methoxymethylpyridine (Compound No. 88) of the formula:

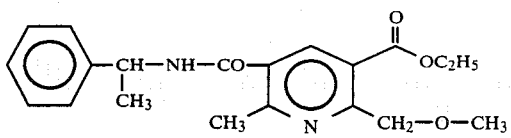

Ethyl 3-amino-4-methoxycrotonate (3.8 g), (S)-N-(α-methylbenzyl)-acetoacetamide (6 g) and ethanol (50 ml) are introduced into a 250 ml three-necked round-bottomed flask. After dissolution of the reactants, a 30% strength (weight/volume) aqueous solution of formaldehyde (4 ml; i.e. about 40 millimols) is added. The reaction has ended after refluxing for one hour at about 80° C. After cooling, the reaction medium is concentrated and then dissolved in acetone (200 ml). It is oxidised by adding an aqueous solution of potassium permanganate (4 g; 25 millimols) in water (100 ml).

When the reaction has ended, the manganese dioxide formed is filtered off and rinsed with methanol. The organic phase is concentrated and then filtered on silica (150 g), elution being carried out with a mixture of equal proportions of ethyl acetate and hexane.

This yields the expected product (32 g) in the form of a yellow viscous oil.

Yield: 38%.

The ethyl 3-amino-4-methoxycrotonate used as the starting material was prepared by reacting concentrated ammonia solution with ethyl methoxyacetate in ethanol.

The ethyl methoxyacetate was prepared as indicated below:

Ethyl tert.-butyl malonate (47 g), prepared according to Organic Syntheses, Coll. Volume IV, page 417, is placed in a 1 l three-necked round-bottomed flask equipped with a mechanical stirrer, a thermometer, a condenser and a dropping funnel. Ethyl ether (350 ml) and then magnesium ethylate (28.5 g; 0.25 mol) are added thereto. After stirring for one hour under reflux, methoxyacetyl chloride is added slowly, the reaction medium being cooled to a temperature of about 20° C. After the addition has ended, the medium is heated under reflux for 1 hour.

After cooling to 10° C., hydrolysis is carried out with 2 N sulphuric acid (150 ml). The organic phase is decanted, washed with sodium bicarbonate, water and sodium chloride solution, and then dried over sodium sulphate. After concentration, the oil obtained is dissolved in toluene (500 ml). Para-toluenesulphonic acid (1 g) is added thereto and the mixture is heated under reflux until the evolution of isobutene and carbon dioxide has ended. After cooling, washing with sodium bicarbonate and drying over sodium sulphate, the organic phase is concentrated and then distilled under a waterpump vacuum.

This yields Compound No. 88 (12 g).
Yield: 30%.

EXAMPLE 6

Preparation of (S)-3-[N-(α-methylbenzyl)-carbamoyl]-5-cyanomethyl-2,6-dimethylpyridine (Compound No. 89) of the formula:

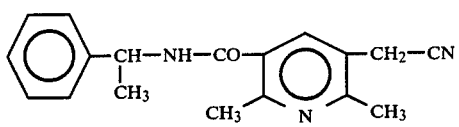

This preparation is carried out in several steps starting from the (S)-3-[N-(α-methylbenzyl)-carbamoyl]-5-methoxycarbonyl-2,6-dimethylpyridine described above as Compound No. 78.

Anydrous tetrahydrofuran (500 ml) and then lithium aluminium hydride (14 g) are introduced into a three-necked round-bottomed flask with a central methanical stirrer, a condenser, a thermometer and a dropping funnel. After cooling to between 5 and 10° C., Compound No. 78 (50 g) in tetrahydrofuran (300 ml) is run in slowly. After the addition has ended, the reaction medium is stirred for 45 minutes at 25°–30° C. After cooling, the reaction medium is hydrolysed with water (14 ml), a 15% strength aqueous solution of sodium hydroxide (14 ml) and finally water (42 ml). The organic phase is dried over sodium sulphate and then filtered; this yields (S)-3-[N-(α-methylbenzyl)-carbamoyl]-5-hydroxymethyl-2,6-dimethylpyridine (45 g), melting at 141° C.

The 5-hydroxymethylpyridine obtained above (45 g), in methylene chloride (one liter), is introduced into a three-necked round-bottomed flask with a dropping funnel, a central methanical stirrer, a condenser and a thermometer. Thionyl chloride (32 g) is run in and the mixture is heated for 30 minutes under reflux.

After cooling, the mixture is neutralised with 4N sodium hydroxide solution (170 ml). After decantation, drying and concentration of the organic phase, (S)-3-[N-(α-methylbenzyl)-carbamoyl]-5-chloromethyl-2,6-dimethylpyridine (37.6 g), melting at 165° C., is obtained after purification.

In a 1 liter Erlenmeyer flask, the 5-chloromethylpyridine obtained above (12 g) is dissolved in ethanol (500 ml) under the action of heat (50° C.).

A solution of sodium cyanide (5.8 g) in water (100 ml) is then run in.

After 24 hours at 50° C., the mixture is concentrated in vacuo and methylene chloride (300 ml) and water (100 ml) are then added. The organic phase is decanted, dried over sodium sulphate and concentrated. The product obtained is filtered on silica (150 g), elution being carried out with a methylene chloride/ethyl ether/methanol mixture (10/10/1). This gives (S)-3-[N-(α-methylbenzyl)-carbamoyl]-5-cyanomethyl-2,6-dimethylpyridine (Compound No. 89) (10.2 g) in the form of white crystals melting at 146° C. Yield: 82% (from the 5-chloromethylpyridine).

EXAMPLE 7

Preparation of (S)-3-[N-(α-methylbenzyl)-carbamoyl]-5-methoxymethyl-2,6-dimethylpyridine (Compound No. 90) of the formula:

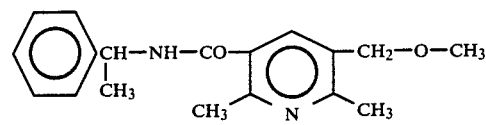

In a 250 ml round-bottomed flask, (S)-3-[N-(α-methylbenzyl)-carbamoyl]-5-chloromethyl-2,6-dimethylpyridine (21 g), the preparation of which is described in Example 6, is introduced into anhydrous methanol (50 ml). After dissolution, a solution of sodium (5.00 g) in methanol (50 ml) is run in.

The reaction has ended after 2 hours under reflux. The mixture is concentrated and then redissolved in methylene chloride (200 ml) and water (100 ml). The organic phase is decanted, dried and concentrated. This yields the desired product (1.8 g), melting at 125° C.

EXAMPLE 8

(S)-3-[N-(α-Methylbenzyl)-carbamoyl]-5-ethoxymethyl2,6-dimethylpyridine (Compound No. 91), melting at 130° C., was prepared by following the method of Example 7, using the appropriate starting materials.

EXAMPLE 9

Herbicidal Application in the Pre-emergence Treatment of Plant Species

A number of seeds are sown in 9×9×9 cm pots filled with light agricultural earth, this number being determined as a function of the plant species and the size of the seed.

The seeds are then covered with an approximately 3 mm thick layer of earth.

After moistening the earth, the pots are treated by spraying with an amount of spraying mixture which corresponds to an application dose of 500 l/ha and contains the active ingredient at the relevant concentration.

The spraying mixture was prepared by diluting, with an amount of water determined so as to obtain the desired concentration, a wettable powder having the following composition by weight:
  active ingredient to be tested—20%
  solid inert carrier: kaolinite—69%
  surface-active agent (deflocculant): calcium lignosulphonate—5%
  surface-active agent (wetting agent): sodium isopropylnaphthalenesulphonate—1%
  anti-caking silica—5%

This wettable powder was obtained by mixing and grinding the ingredients in a microniser so as to obtain an average particle size of less than 40 microns.

The dose of active ingredient applied was 0.5 to 8 kg/ha, according to the concentration of active ingredient in the spraying mixture.

The treated pots are then placed in troughs which are intended to receive the moistening water, by subirrigation, and are kept for 35 days at ambient temperature under 70% relative humidity.

After 35 days, the number of living plants in the pots treated with the spraying mixture containing the active ingredient to be tested, and the number of living plants in a control pot treated under the same conditions, but with a spraying mixture not containing active ingredient, are counted. The percentage destruction of the treated plants, relative to the untreated control, is thus determined. A percentage destruction of 100% indicates that there has been complete destruction of the plant species in question, and a percentage of 0% indicates that the number of living plants in the treated pot is identical to that in the control pot.

For the experiments of this example, the plant species used were as follows:

|  | Abbreviation used |
|---|---|
| Monocotyledon adventitious plants: | |
| Wild oat (*Avena fatua*) | WO |
| Finger grass (*Digitaria sanguinalis*) | FIN |
| Panic grass (*Echinochloa crus-galli*) | PAN |
| Ray grass (*Lolium multiflorum*) | RAY |
| Foxtail grass (*Setaria faberii*) | FOX |
| Slender foxtail (*Alopecurus myosuroides*) | SF |
| Dicotyledon adventitious plants: | |
| Goosefoot (Chenopodium sp) | GOO |
| Corn marigold (*Chrysanthemum segetum*) | CM |
| Black nightshade (*Solanum nigrum*) | BN |
| Wild mustard (*Sinapis arvensis*) | WM |
| Chickweed (*Stellaria media*) | CHI |
| Monocotyledon crops: | |
| Wheat (*Triticum sativum*) | WHE |
| Maize (*Zea mays*) | MAI |
| Four-row barley (*Hordeum vulgare*) | BAR |
| Rice (*Oryza sativa*) | RIC |
| Dicotyledon crops: | |
| Rapeseed (*Brassica oleracea*) | RAP |
| Cotton (*Gossypium barbadense*) | COT |
| Bean (*Phaseolus vulgaris*) | BEA |
| Soya bean (*Glycine max*) | SOY |
| Sunflower (*Helianthus annuus*) | SUN |

The results observed are indicated in the tables in the following manner (application in a pre-emergence treatment):

Table (VI)—adventitious plants—products of the formula (II)

Table (VII)—crops—products of the formula (II)

Table (VIII)—adventitious plants—products of the formula (III)

Table (IX)—crops—products of the formula (III).

EXAMPLE 10

Herbicidal Application in the Post-Emergence Treatment of Plant Species

A number of seeds are sown in 9×9×9 cm pots filled with light agricultural earth, this number being determined as a function of the plant species and the size of the seed.

The seeds are then covered with an approximately 3 mm thick layer of earth and the seed is left to germinate until it produces a plantlet of 5 to 10 cm in height.

The pots are then treated by spraying with an amount of spraying mixture which corresponds to an application dose of 500 l/ha and contains the active ingredient at the relevant concentration.

The spraying mixture was prepared in the same manner as in Example 9.

The dose of active ingredient applied was 2 to 8 kg/ha, according to the concentration of active ingredient in the spraying mixture.

The treated pots are then placed in troughs which are intended to receive the moistening water, by subirrigation, and are kept for 30 days at ambient temperature under 70% relative humidity.

After 30 days, the number of living plants in the pots treated with the spraying mixture containing the active ingredient to be tested, and the number of living plants in a control pot treated under the same conditions, but with a spraying mixture not containing active ingredient, are counted. The percentage destruction of the treated plants, compared with the untreated control, is thus determined. A percentage destruction of 100% indicates that there has been complete destruction of the plant species in question, and a percentage of 0% indicates that the number of living plants in the treated pot is identical to that in the control pot.

The name and the abbreviation of the plant species used are as indicated above.

The results observed are indicated in Tables (X) and (XII) for the products of the formula (II) and in Tables (XI) and (XII) for the products of the formula (III).

The results obtained in the above examples and reported in Tables (VI) to (XII) show the excellent herbicidal activity of the compounds according to the invention on the majority of the adventitious plants treated, both graminaceous and dicotyledon plants, and also their selectivity with respect to the crops in question.

For their use in practice, the compounds according to the invention are rarely employed by themselves. Most frequently, they form part of compositions. These compositions, which can be used as herbicidal agents, contain, as the active ingredient, a compound according to the invention, such as described above, in combination with the solid or liquid carriers acceptable in agriculture and the surface-active agents also acceptable in agriculture. In particular, it is possible to use the customary inert carriers and the customary surface-active agents.

These compositions can also contain all kinds of other ingredients, such as e.g. protective colloids, adhesives, thickeners, thixotropic agents, penetrating agents, stabilisers, sequestering agents and the like, and also other known active ingredients having pesticidal properties (in particular insecticides, fungicides or herbicides) or properties which favour plant growth (in particular fertilizers) or properties which regulate plant growth. More generally, the compounds according to the invention can be combined with all the solid or liquid additives corresponding to the usual formulation techniques.

The use doses of the compounds according to the invention can vary within wide limits, in particular according to the nature of the adventitious plants to be eliminated and the usual degree of infestation of the crops by these adventitious plants.

In general, the compositions according to the invention usually contain from about 0.05 to 95% (by weight) of one or more compounds according to the invention, from about 1% to 94.95% of one or more solid or liquid carriers and, if appropriate, from about 0.1 to 20% of one or more surface-active agents.

In accordance with what has already been stated, the compounds according to the invention are generally used in combination with carriers and, if appropriate, surface-active agents.

In the present account, the term "carrier" denotes an organic or inorganic, natural or synthetic material with which the active ingredient is combined in order to facilitate its application to the plant, to seeds or to the soil. This carrier is therefore generally inert and it must be agriculturally acceptable, in particular on the plant treated. The carrier can be solid (clays, natural or synthetic silicates, silica, resins, waxes, solid fertilizers and the like) or liquid (water, alcohols, ketones, petroleum fractions, aromatic or paraffinic hydrocarbons, chlorohydrocarbons, liquefied gases and the like).

The surface-active agent can be an emulsifying, dispersing or wetting agent of ionic or non-ionic type. Examples which may be mentioned are salts of polyacrylic acids, salts of lignosulphonic acids, salts of phenol-sulphonic or naphthalenesulphonic acids, polycondensates of ethylene oxide with fatty alcohols, fatty acids or fatty amines, substituted phenols (in particular alkyl-phenols or arylphenols), salts of sulphosuccinic acid esters, taurine derivatives (in particular alkyl-taurates) and phosphoric acid esters of condensates of ethylene oxide with alcohols or phenols. The presence of at least one surface-active agent is generally essential if the active ingredient and/or the inert carrier are not soluble in water and if the vehicle of application is water.

For their application, the compounds of the formula (I) are therefore generally in the form of compositions; these compositions according to the invention are themselves in a fairly wide variety of solid or liquid forms.

As forms of solid compositions, there may be mentioned dusting powders or sprinkling powders (with a content of compound of the formula (I) which can range up to 100%) and granules, in particular those obtained by extrusion, by compaction, by the impregnation of a granular carrier or by the formation of granules from a powder (the content of compound of the formula (I) in these granules being between 0.5 and 80% for these last cases).

As forms of liquid compositions or compositions which are to be made up into liquid compositions on application, there may be mentioned suspension concentrates, wettable powders (or spraying powders) and pastes.

The suspension concentrates, which can be applied by spraying, are prepared so as to give a stable fluid product which does not form a deposit, and they usually contain from 10 to 75% of active ingredient, from 0.5 to 15% of surface-active agents, from 0.1 to 10% of thixotropic agents, from 0 to 10% of suitable additives, such as anti-foam agents, corrosion inhibitors, stabilisers, penetrating agents and adhesives, and, as the carrier, water or an organic liquid in which the active ingredient is sparingly soluble or insoluble; certain organic solids, or organic salts, can be dissolved in the carrier in order to assist in preventing sedimentation or to act as anti-freeze agents for the water.

The wettable powders (or spraying powders) are usually prepared so as to contain 20 to 95% of active ingredient, and they usually contain, in addition to the solid carrier, from 0 to 5% of a wetting agent, from 3 to 10% of a dispersing agent and, where necessary, from 0 to 10% of one or more stabilisers and/or other additives, such as penetrating agents, adhesives, anti-caking agents, dyestuffs and the like.

Various compositions of wettable powders are now given as examples:
 active ingredient: 50%
 calcium lignosulphonate (deflocculant): 5%
 isopropylnaphthalenesulphonate (anionic wetting agent): 1%
 anti-caking silica: 5%
 kaolin (filler): 39%

Another example of a wettable powder, this time of 80% strength, is given below:
 active ingredient: 80%
 sodium alkylnaphthalenesulphonate: 2%
 sodium lignosulphonate: 2%
 anti-caking silica: 3%
 kaolin: 13%

Another example of a wettable powder is given below:
 active ingredient: 50%
 sodium alkylnaphthalenesulphonate: 2%
 low-viscosity methylcellulose: 2%
 diatomaceous earth: 46%

Another example of a wettable powder is given below:
 active ingredient: 90%
 sodium dioctylsulphosuccinate: 0.2%
 synthetic silica: 9.8%

Another composition of a spraying powder, this time of 70% strength, uses the following constituents:
 active ingredient: 700 g
 sodium dibutylnaphthylsulphonate 50 g
 3:2:1 naphthalenesulphonic acid/phenolsulphonic acid/formaldehyde condensate: 30 g
 kaolin: 100 g
 Champagne chalk: 120 g Another composition of a spraying powder, this time of 40% strength the following constituents:
 active ingredient: 400 g
 sodium lignosulphonate 50 g
 sodium dibutylnaphthalenesulphonate: 10 g
 silica: 540 g Another composition of a spraying powder, this time of 25% strength, uses the following constituents:
 active ingredient: 250 g
 calcium lignosulphonate: 45 g
 mixture of equal parts by weight of Champagne chalk and hydroxyethylcellulose: 19 g
 soium dibutylnaphthalenesulphonate: 15 g
 silica: 195 g
 Champagne chalk: 195 g
 kaolin: 281 g Another composition of a 25% strength spraying powder uses the following constituents:
 active ingredient 250 g
 isooctylphenoxy-polyoxyethylene-ethanol: 25 g
 mixture of equal parts by weight of Champagne chalk and hydroxyethylcellulose: 17 g
 sodium aluminosilicate: 543 g
 kieselguhr: 165 g Another composition of a spraying powder, this time of 10% strength, uses the following constituents:
 active ingredient: 100 g
 mixture of sodium salts of saturated fatty acid sulphates: 30 g
 naphthalenesulphonic acid/formaldehyde condensate: 50 g
 kaolin: 820 g To obtain these spraying powders or wettable powders, the active ingredients are intimately mixed with the additional substances in suitable mixers, and the mixture is ground in mills or other suitable grinders. This gave spraying powders of advantageous wettability and suspendability; they can be suspended in water at any desired concentration. and this suspension can be used very advantageously, in particular for application to the leaves of the plants.

In place of the wettable powders, it is possible to produce pastes. The conditions and modes of production and use of these pastes are similar to those of the wettable powders or spraying powders.

As already stated, the dispersions, e.g. the compsitions obtained by diluting, with water, a wettable powder according to the invention, are included within the general scope of the present invention. The term "spraying mixture" is used to denote the compositions diluted with water, in the form in which they are applied to the crops.

All these aqueous dispersions or aqueous emulsions, or spraying mixtures, can be applied by any suitable means, mainly by spraying to the crops in which weeds are to be destroyed, at doses which are generally of the order of 100 to 1,200 liters of spraying mixture per hectare.

The granules, which are intended to be placed on the soil, are usually prepared so as to have sizes of between 0.1 and 2 mm, and they can be manufactured by agglomeration or impregnation. Preferably, the granules contain 1 to 25% of active ingredient and 0 to 10% of additives, such as stabilisers, slow-release modifiers, binders and solvents.

According to one example of the composition of granules, the following constituents are used:
  active ingredient: 50 g
  epichlorohydrin: 2.5 g
  cetyl polyglycol ether: 2.5 g
  polyethylene glycol: 35 g
  kaolin (particle size: 0.3 to 0.8 mm): 910 g In this particular case, the active ingredient is mixed with the epichlorohydrin and the mixture is disperesed in acetone (60 g); the polyethylene glycol and the cetyl polyglycol ether are then added. The kaolin is wetted with the dispersion obtained and the acetone is then evaporated off in vacuo.

As indicated above, the invention also relates to a process for destroying weeds in crops, in particular cotton, sunflower, wheat and barley, wherein an effective amount of at least one of the compounds according to the invention is applied to the plants and/or to the soil in the zone in which weeds are to be destroyed. In practice, these compounds are used in the form of the herbicidal composition according to the invention, which have been described above. In general, amounts of active ingredient ranging from 0.1 to 10 kg/ha give good results, it being understood that the choice of the amount of active ingredient to be used depends on the intensity of the problem to be solved, the climatic conditions and the crop in question. The treatment is generally carried out as a pre-emergence treatment of the crops and adventitious plants, or as a pre-sowing treatment of the crops with incorporation into the soil (this incorporation is therefore a complementary operation to the treatment process of the invention), although, in certain cases, depending on the compound used, good results can also be obtained by post-emergence treatments. Other embodiments of the treatment process according to the invention can also be used: thus, it is possible to apply the active ingredient to the soil, with or without incorporation, before planting out a crop.

The treatment process of the invention is applied both in the case of annual crops and in the case of perennial crops; in the latter case, it is preferred to apply the active ingredients of the invention in a localised manner, e.g. between the rows of the said crops.

TABLE (I)

Compounds of the formula (II).
$R^1 = H$; $R^2 = R^3 = -CH_3$; $R^4 = -COOR^8$; $R^5 = R^6 = H$

| Compound No. | $R^8$ | $(R^7)_n$-C$_6$H$_4$- | M.p. in °C. | Yield in % |
|---|---|---|---|---|
| 1 | —CH$_3$ | C$_6$H$_5$— | 156 | 17 |
| 2 | —C$_2$H$_5$ | C$_6$H$_5$— | 101 | 49 |
| 3 | —CH$_3$ | p-CH$_3$—C$_6$H$_4$— | 186 | 11 |
| 4 | —C$_2$H$_5$ | p-CH$_3$—C$_6$H$_4$— | 135 | 30 |
| 5 | —C$_2$H$_5$ | m-CH$_3$O—C$_6$H$_4$— | 119 | 23 |
| 6 | —C$_2$H$_5$ | p-CH$_3$O—C$_6$H$_4$— | 114 | 22 |
| 7 | —CH$_3$ | o-Cl—C$_6$H$_4$— | 128 | 30 |
| 8 | —C$_2$H$_5$ | o-Cl—C$_6$H$_4$— | 134 | 30 |
| 9 | —CH$_3$ | m-Cl—C$_6$H$_4$— | 162 | 25 |
| 10 | —C$_2$H$_5$ | m-Cl—C$_6$H$_4$— | 130 | 20 |
| 11 | —CH$_3$ | p-Cl—C$_6$H$_4$— | 184 | 23 |
| 12 | —C$_2$H$_5$ | p-Cl—C$_6$H$_4$— | 145 | 28 |
| 13 | —CH$_3$ | o-F—C$_6$H$_4$— | 155 | 15 |
| 14 | —CH$_3$ | p-F—C$_6$H$_4$— | 178 | 8 |
| 15 | —C$_2$H$_5$ | p-F—C$_6$H$_4$— | 144 | 25 |
| 16 | —C$_2$H$_5$ | o,p-Cl$_2$C$_6$H$_3$— | 151 | 18 |
| 17 | —C$_2$H$_5$ | m,p-Cl$_2$C$_6$H$_3$— | 133 | 28 |
| 18 | —C$_2$H$_5$ | m-CF$_3$—C$_6$H$_4$— | 165 | 11 |
| 19 | —CH$_3$ | 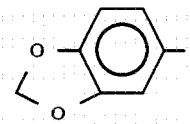 | 157 | 14 |

TABLE (II)

Compounds of the formula (II).
$R^1 = H$; $R^2 = R^3 = -CH_3$; $R^4 = -COOR^8$; $R^5 = H$; $R^6 = -CH_3$
dl, l and d respectively denote racemic, laevorotatory and dextrorotatory

| Compound No. | $R^8$ | $(R^7)_n$-C$_6$H$_4$- | Optical isomerism of the starting amine | M.p. in °C. | Yield in % |
|---|---|---|---|---|---|
| 20 | —CH$_3$ | C$_6$H$_5$— | dl | 186 | 19 |
| 21 | —CH$_3$ | C$_6$H$_5$— | l | 180 | 13 |
| 22 | —C$_2$H$_5$ | C$_6$H$_5$— | l | 139 | 19 |
| 23 | —C$_2$H$_5$ | C$_6$H$_5$ | d | 145 | 10 |
| 24 | —C$_2$H$_5$ | C$_6$H$_5$— | dl | | |
| 25 | —CH$_3$ | o-CH$_3$—C$_6$H$_4$ | dl | 145 | 13 |
| 26 | —C$_2$H$_5$ | p-Cl—C$_6$H$_4$— | dl | 163 | 21 |
| 27 | —C$_2$H$_5$ | p-F—C$_6$H$_4$— | dl | 167 | 35 |
| 28 | —C$_2$H$_5$ | o,p-Cl$_2$C$_6$H$_3$— | dl | 123 | 25 |
| 29 | —C$_2$H$_5$ | m,p-Cl$_2$C$_6$H$_3$— | dl | 126 | 20 |

TABLE (III)

Compounds of the formula (II).
$R^1 = H$; $R^2 = R^3 = -CH_3$; $R^4 = COOR^8$

| Compound No. | $R^8$ | $(R^7)_n$-C$_6$H$_4$-C(R$^5$)(R$^6$)- | M.p. in °C. | Yield in % |
|---|---|---|---|---|
| 30 | —C$_2$H$_5$ | C$_6$H$_5$—CH—CH—(CH$_3$)$_2$ | 100 | 36 |
| 31 | —C$_2$H$_5$ | C$_6$H$_5$—C(CH$_2$—CH$_2$)— | 139 | 13 |

TABLE (IV)

Compounds of the formula (III).
$R^1 = H; R^2 = R^3 = -CH_3; R^4 = -COOR^8$

| Compound No. | $R^8$ | $R^5$ | $R^6$ | $(R^7)_n$-⬡- | M.p. in °C. | Yield in % during the preparation |
|---|---|---|---|---|---|---|
| 51 | $-C_2H_5$ | H | H | o-Cl—$C_6H_4$— | 134 | 80 |
| 52 | $-CH_3$ | H | H | o-Cl—$C_6H_4$— | 129 | 70 |
| 53 | $-C_2H_5$ | H | H | m-Cl—$C_6H_4$— | 117 | 60 |
| 54 | $-C_2H_5$ | H | H | p-F—$C_6H_4$— | 132 | 40 |
| 55 | $-C_2H_5$ | H | $-CH_3$ | p-Cl—$C_6H_4$— | 150 | 51 |
| 56 | $-C_2H_5$ | H | H | m-CF$_3$—$C_6H_4$— | 144 | 28 |
| 57 | $-C_2H_5$ | \_CH$_2$—CH$_2$_/ | | $C_6H_5$— | 118 | 43 |
| 58 | $-C_2H_5$ | H | H | p-Cl—$C_6H_4$ | 133 | 32 |
| 59 | $-C_2H_5$ | H | $-CH_3$ | $C_6H_5$— | 90 | 15 |
| 60 | $-C_2H_5$ | $-CH_3$ | H | $C_6H_5$— | 86 | 32 |
| 61 | $-C_2H_5$ | H | $-CH_3$ | o-CH$_3$—$C_6H_4$— | 113 | 63 |
| 62 | $-C_2H_5$ | H | $-CH_3$ | o,p-Cl$_2$C$_6$H$_3$— | 135 | 56 |
| 63 | $-CH_3$ | H | $-CH_3$ | o-CH$_3$—$C_6H_4$— | 177 | 89 |
| 64 | $-CH_3$ | H | H | p-F—$C_6H_4$ | 107 | 30 |
| 65 | $-C_2H_5$ | H | $-CH_3$ | p-F—$C_6H_4$— | 62 | 59 |
| 66 | $-C_2H_5$ | H | $-CH_3$ | m,o-Cl$_2$C$_6$H$_3$— | 132 | 58 |

TABLE (V)

Compounds of the formula (III). $R^1 = H; R^2 = R^3 = -CH_3; R^4 = -COOR^8$

| Compound No. | $R^8$ | $R^5$ | $R^6$ | $(R^7)_n$-⬡- | $R^2$ | M.p. in °C. | Yield in % during the preparation |
|---|---|---|---|---|---|---|---|
| 67 | $-C_2H_5$ | H | H | m-p-Cl$_2$C$_6$H$_3$— | $-CH_3$ | 129 | 54 |
| 68 | $-C_2H_5$ | H | H | p-CH$_3$—$C_6H_4$— | $-CH_3$ | 145 | 47 |
| 69 | $-C_2H_5$ | H | H | o-p-Cl$_2$C$_6$H$_3$— | $-CH_3$ | 149 | 62 |
| 70 | $-CH_3$ | H | $-CH_3$ | $C_6H_5$— | $-CH_3$ | 129 | 46 |
| 71 | $-C_2H_5$ | H | $-CH_3$ | 2,5-dichlorophenyl | $-CH_3$ | 160 | 9 |
| 72 | $-C_2H_5$ | H | H | m-CH$_3$O—$C_6H_4$— | $-CH_3$ | 136 | 56 |
| 73 | $-C_2H_5$ | H | H | p-CH$_3$O—$C_6H_4$— | $-CH_3$ | 132 | 95 |
| 74 | $-C_2H_5$ | $-CH_3$ | $-CH_3$ | $C_6H_5$— | $-CH_3$ | 137 | 35 |
| 75 | $-C_2H_5$ | H | H | $C_6H_5$— | $-CH_3$ | 99 | 53 |
| 76 | $-C_2H_5$ | H | $-CH_3$ | $C_6H_5$— | $-CH_3$ | 122 | 30 |
| 77 | $-CH_3$ | H | H | $C_6H_5$— | $-CH_3$ | 107 | 50 |
| 78 | $-CH_3$ | H | $-CH_3$ | $C_6H_5$— | $-CH_3$ | 116 | 32 |
| 79 | $-CH_3$ | H | H | p-Cl—$C_6H_4$— | $-CH_3$ | 156 | 42 |
| 80 | $-CH_3$ | H | H | m-Cl—$C_6H_4$— | $-CH_3$ | 165 | 38 |
| 81 | $-CH_3$ | H | H | o-F—$C_6H_4$— | $-CH_3$ | 130 | 32 |
| 82 | $-CH_3$ | H | H | O—CH$_2$—O-⬡- (methylenedioxyphenyl) | $-CH_3$ | 152 | 28 |
| 83 | $-CH_3$ | H | H | m-F—$C_6H_4$— | $-CH_3$ | 149 | 40 |
| 84 | $-C_2H_5$ | H | H | o-CH$_3$O—$C_6H_4$ | $-CH_3$ | 109 | 36 |
| 85 | $-CH_3$ | H | H | $C_6H_5$— | $-C_2H_5$ | 126 | 24 |
| 86 | $-CH_3$ | H | H | m-NO$_2$—$C_6H_4$— | $-CH_3$ | 183 | 43 |
| 87 | $-CH_3$ | H | H | p-CH$_3$—$C_6H_4$— | $-CH_3$ | 146 | 34 |

Compounds of the formula (III). $R^1 = H, R^2 = -CH_3, R^5 = H, R^6 = -CH_3, n = $ zero

| Compound No. | $R^3$ | $R^4$ | M.p. in °C. | Yield in % during the preparation |
|---|---|---|---|---|
| 88 | $-CH_2-O-CH_3$ | $-COOC_2H_5$ | oil | 30 |
| 89 | $-CH_3$ | $-CH_2-CN$ | 146 | 88 |
| 90 | $-CH_3$ | $-CH_2-O-CH_3$ | 125 | 86 |
| 91 | $-CH_3$ | $-CH_2-O-C_2H_5$ | 130 | 76 |

TABLE (VI)

| Compound No. | Dose kg/ha | ADVENTITIOUS PLANTS (pre-emergence treatment) | | | | | | | | | | |
|---|---|---|---|---|---|---|---|---|---|---|---|---|
| | | WO | FIN | PAN | RAY | FOX | SF | GOO | BN | WM | CHI | CM |
| 1 | 8 | 100 | | 100 | 100 | | | 100 | | 100 | | |
|  | 2 | 0 | 100 | 50 | 80 | 100 | 90 | 100 | 98 | 85 | 100 | 30 |
| 2 | 8 | 100 | | 100 | 100 | | | 100 | | 100 | | |
|  | 2 | 0 | 100 | 0 | 0 | 100 | 10 | 100 | 100 | 100 | 100 | 90 |
|  | 0.5 | 0 | 100 | 0 | 0 | 80 | 0 | 98 | 100 | 0 | 90 | 80 |
| 4 | 2 | 20 | 90 | 30 | | | | 100 | | 100 | | |
| 5 | 1 | 20 | | 95 | 80 | | | 100 | | 100 | | |
| 6 | 1 | 20 | | 100 | 90 | | | 100 | | 100 | | |
| 7 | 8 | 100 | | 100 | 100 | | | 100 | | 100 | | |
|  | 2 | 0 | 100 | 50 | 90 | 100 | 98 | 100 | 100 | 0 | 100 | 90 |
| 8 | 8 | 95 | | 100 | 100 | | | 100 | | 100 | | |
|  | 1 | 0 | 100 | 0 | 0 | 100 | 0 | 100 | 100 | 98 | 100 | 60 |
| 10 | 8 | 95 | | 100 | 100 | | | 100 | | 100 | | |
|  | 2 | 0 | 100 | 80 | 80 | 100 | 60 | 100 | 100 | 20 | 100 | 95 |
| 12 | 8 | 100 | | 100 | 100 | | | 100 | | 100 | | |
|  | 1 | 0 | 100 | 50 | 30 | 98 | 30 | 100 | 100 | 0 | 100 | 80 |
|  | 0.5 | 0 | 100 | 0 | 0 | 98 | 10 | 100 | 100 | 0 | 100 | 60 |
| 13 | 8 | 70 | | 90 | 100 | | | 100 | | 100 | | |
| 14 | 8 | 100 | | 100 | 100 | | | 100 | | 100 | | |
| 15 | 8 | 100 | | 100 | 100 | | | 100 | | 100 | | |
|  | 1 | 0 | 100 | 60 | 60 | 100 | 80 | 100 | 100 | 90 | 100 | 95 |
| 16 | 6 | 70 | | 100 | 98 | | | 100 | | 100 | | |
|  | 1 | 0 | 100 | 0 | 0 | 98 | 10 | 100 | 98 | 0 | 100 | 0 |
| 17 | 2 | 20 | | 50 | 30 | | | 100 | | 100 | | |
|  | 1 | 0 | 98 | 0 | 0 | 80 | 0 | 100 | 100 | 0 | 100 | 0 |
| 18 | 8 | 100 | | 100 | 100 | | | 100 | | 100 | | |
| 21 | 1 and 8 | 100 | | 100 | 100 | | | 100 | | 100 | | |
| 22 | 8 | 100 | | 100 | 100 | | | 100 | | 100 | | |
|  | 0.5 | 10 | 100 | 90 | 40 | 100 | 70 | 100 | 100 | 85 | 100 | 90 |
| 23 | 8 | 20 | | 90 | 20 | | | 100 | | 70 | | |
|  | 4 | 0 | 100 | 15 | 0 | 100 | 0 | 100 | 100 | 10 | 60 | 80 |
| 24 | 8 | 100 | | 100 | 100 | | | 100 | | 100 | | |
|  | 1 | 5 | 100 | 90 | 80 | 100 | 60 | 100 | 100 | 60 | 100 | 90 |
| 25 | 8 | 80 | | 100 | 100 | | | 100 | | 100 | | |
| 26 | 8 | 100 | | 100 | 100 | | | 100 | | 100 | | |
|  | 1 | 0 | 100 | 80 | 50 | 100 | 80 | 100 | 100 | 98 | 100 | 90 |
| 27 | 2 | 90 | | 100 | 95 | | | 100 | | 100 | | |
| 28 | 8 | 90 | | 100 | 70 | | | 100 | | 100 | | |
|  | 0.5 | 0 | 95 | 0 | 0 | 95 | 10 | 98 | 100 | 0 | 100 | 0 |
| 29 | 8 | 20 | | 100 | 20 | | | 100 | | 100 | | |
|  | 2 | 0 | 100 | 20 | 0 | 98 | 5 | 100 | 100 | 0 | 100 | 0 |
| 30 | 8 | 0 | | 20 | 20 | | | 100 | | 30 | | |
| 31 | 8 | 100 | | 100 | 100 | | | 100 | | 100 | | |
|  | 0.5 | 0 | 100 | 20 | 30 | 100 | 20 | 100 | 100 | 70 | 100 | 70 |

TABLE (VII)

| Compound No. | Dose kg/ha | CROPS (pre-emergence treatment) | | | | | | | | |
|---|---|---|---|---|---|---|---|---|---|---|
| | | WHE | MAI | BAR | RIC | RAP | COT | BEA | SOY | SUN |
| 1 | 8 | | | | | | | 0 | | |
|  | 2 | 30 | 5 | 5 | 0 | | 0 | 0 | 20 | 0 |
| 2 | 8 | | | | | | | 50 | | |
|  | 2 | 0 | 0 | 0 | 0 | | 0 | 0 | 0 | 0 |
|  | 0.5 | 0 | 0 | 0 | 0 | 10 | 0 | 0 | 0 | 0 |
| 4 | 2 | | | | | | | 0 | | |
| 5 | 1 | | | | | | | 0 | | |
| 6 | 1 | | | | | | | 30 | | |
| 7 | 8 | | | | | | | 0 | | |
|  | 2 | 0 | 10 | 0 | 0 | | 0 | 0 | 0 | 0 |
| 8 | 8 | | | | | | | 0 | | |
|  | 1 | 0 | 0 | 0 | 0 | | 0 | 0 | 0 | 0 |
| 10 | 8 | | | | | | | 0 | | |
|  | 2 | 0 | 10 | 5 | 15 | | 0 | 0 | 0 | 0 |
| 12 | 8 | | | | | | | 100 | | |
|  | 1 | 0 | 0 | 10 | 0 | 0 | 0 | 0 | 0 | 0 |
|  | 0.5 | 0 | 0 | 0 | 5 | 10 | 0 | 0 | 0 | 0 |
| 13 | 8 | | | | | | | 0 | | |
| 14 | 8 | | | | | | | 100 | | |
| 15 | 8 | | | | | | | 30 | | |
|  | 1 | 0 | 0 | 0 | 10 | 20 | 0 | 30 | 5 | 0 |
| 16 | 8 | | | | | | | 0 | | |
|  | 1 | 0 | 0 | 0 | 0 | 0 | 0 | 0 | 0 | 0 |
| 17 | 4 | 0 | 0 | 0 | 5 | | 0 | 0 | 20 | 0 |
|  | 1 | 0 | 0 | 0 | 0 | 5 | 0 | 0 | 20 | 0 |
| 22 | 8 | | | | | | | | | |
|  | 0.5 | 10 | 30 | 0 | 10 | | 0 | 30 | 0 | 0 |
| 23 | 8 | | | | | | | 30 | | |
|  | 4 | 0 | 0 | 0 | 0 | | 30 | 0 | 50 | 0 |

TABLE (VII)-continued

| Compound No. | Dose kg/ha | CROPS (pre-emergence treatment) | | | | | | | | |
|---|---|---|---|---|---|---|---|---|---|---|
| | | WHE | MAI | BAR | RIC | RAP | COT | BEA | SOY | SUN |
| 24 | 8 | | | | | | | 30 | | |
| | 1 | 5 | 10 | 0 | 5 | | 0 | 0 | 20 | 0 |
| 25 | 8 | | | | | | | | | |
| 26 | 1 | 5 | 5 | 0 | 10 | 20 | 0 | 30 | 20 | 0 |
| 27 | 2 | | | | | | | 0 | | |
| 28 | 0.5 | 0 | 0 | 0 | 30 | 5 | 0 | 0 | 20 | 0 |
| 29 | 2 | 0 | 0 | 0 | 10 | | 0 | 0 | 10 | 0 |
| 30 | 8 | | | | | | | 0 | | |
| 31 | 8 | | | | | | | 0 | | |
| | 0.5 | 0 | 0 | 0 | 0 | | 0 | 0 | 0 | 0 |

TABLE (VIII)

| Compound No. | Dose kg/ha | ADVENTITIOUS PLANTS IN PRE-EMERGENCE TREATMENT | | | | | | | | | | |
|---|---|---|---|---|---|---|---|---|---|---|---|---|
| | | WO | FIN | PAN | RAY | FOX | SF | GOO | CM | BN | WM | CHI |
| 51 | 8 | 100 | | 100 | 100 | | | 100 | | | 100 | |
| | 2 | 0 | 100 | 20 | 30 | 100 | 40 | 100 | 95 | 100 | 80 | 100 |
| 52 | 8 | 98 | | 100 | 100 | | | 100 | | | 100 | |
| | 1 | 0 | 100 | 50 | 85 | 100 | 95 | 100 | 80 | 100 | 80 | 100 |
| 53 | 8 | 100 | | 100 | 100 | | | 100 | | | 100 | |
| | 1 | 0 | 100 | 60 | 40 | 100 | 60 | 100 | 80 | 100 | 0 | 100 |
| 54 | 8 | 100 | | 100 | 100 | | | 100 | | | 100 | |
| | 0.5 | 0 | 100 | 40 | 0 | 100 | 20 | 100 | 90 | 100 | 80 | 100 |
| 55 | 8 | 100 | | 100 | 100 | | | 100 | | | 100 | |
| | 0.5 | 0 | 100 | 60 | 15 | 100 | 60 | 100 | 20 | 100 | 90 | 100 |
| 56 | 8 | 95 | | 100 | 100 | | | 100 | | | 100 | |
| 57 | 8 | 100 | | 100 | 100 | | | 100 | | | 100 | |
| | 0.5 | 0 | 100 | 20 | 10 | 100 | 30 | 100 | 30 | 100 | 60 | 100 |
| 58 | 8 | 100 | | 100 | 100 | | | 100 | | | 100 | |
| | 2 | 0 | 100 | 90 | 80 | 100 | 70 | 100 | 95 | 100 | 98 | 100 |
| 59 | 8 | 60 | | 100 | 90 | | | 100 | | | 100 | |
| | 2 | 0 | 100 | 30 | 20 | 100 | 0 | 100 | 60 | 100 | 95 | 100 |
| 60 | 8 | 100 | | 100 | 100 | | | 100 | | | 100 | |
| | 0.5 | 10 | 100 | 95 | 30 | 100 | 80 | 100 | 90 | 100 | 30 | 100 |
| 61 | 8 | 95 | | 100 | 100 | | | 100 | | | 100 | |
| 62 | 8 | 60 | | 100 | 80 | | | 100 | | | 100 | |
| | 0.5 | 0 | 98 | 0 | 10 | 100 | 10 | 100 | 0 | 100 | 0 | 100 |
| 63 | 8 | 95 | | 100 | 60 | | | 100 | | | 100 | |
| 64 | 8 | 100 | | 100 | 100 | | | 100 | | | 100 | |
| | 2 | 95 | | 100 | 100 | | | 100 | | | 100 | |
| 65 | 8 | 100 | | 100 | 100 | | | 100 | | | 100 | |
| | 2 | 98 | | 100 | 100 | | | 100 | | | 100 | |
| 66 | 8 | 40 | | 98 | 40 | | | 100 | | | 100 | |
| | 2 | 20 | | 95 | 20 | | | 100 | | | 100 | |
| | 1 | 0 | 98 | 0 | 0 | 98 | 0 | 100 | 0 | 100 | 0 | 100 |
| 67 | 8 | 50 | | 100 | 90 | | | 100 | | | 100 | |
| | 2 | 20 | | 60 | 20 | | | 100 | | | 100 | |
| 68 | 8 | 70 | | 100 | 85 | | | 100 | | | 100 | |
| | 1 | 20 | | 50 | 20 | | | 100 | | | 100 | |
| 69 | 8 | 100 | | 100 | 100 | | | 100 | | | 100 | |
| | 2 | 0 | 98 | 30 | 15 | 100 | 70 | 100 | 0 | 100 | 0 | 100 |
| | 1 | 30 | | 98 | 70 | | | 100 | | | | |
| 70 | 8 | 100 | | 100 | 100 | | | 100 | | | 100 | |
| | 1 | 60 | | 98 | 100 | | | 100 | | | 100 | |
| 71 | 8 | 10 | | 90 | 10 | | | 100 | | | 100 | |
| 72 | 8 | 90 | | 90 | 100 | | | 100 | | | 100 | |
| | 1 | 10 | | 80 | 80 | | | 100 | | | 100 | |
| 73 | 8 | 60 | | 100 | 100 | | | 100 | | | 100 | |
| | 1 | 20 | | 80 | 80 | | | 100 | | | 95 | |
| 74 | 8 | 10 | | 0 | 80 | | | 100 | | | 80 | |
| 75 | 8 | 95 | | 100 | 95 | | | 100 | | | 100 | |
| | 2 | 0 | 100 | 80 | 30 | 100 | 20 | 100 | 98 | 100 | 100 | 100 |
| 76 | 8 | 100 | | 100 | 100 | | | 100 | | | 100 | |
| | 1 | 10 | 100 | 90 | 60 | 100 | 70 | 100 | 90 | 100 | 100 | 100 |
| 77 | 8 | 0 | | 40 | 20 | | | 100 | | | 0 | |
| 88 | 8 | 100 | | 100 | 100 | | | 100 | | | 100 | |
| | 1 | 60 | | 100 | 100 | | | 100 | | | 100 | |
| 89 | 8 | 100 | | 100 | 100 | | | 100 | | | 100 | |
| | 1 | 95 | | 100 | 95 | | | 100 | | | 100 | |
| 90 | 8 | 100 | | 100 | 100 | | | 100 | | | 100 | |
| | 1 | 95 | | 98 | 98 | | | 100 | | | 98 | |
| 91 | 8 | 60 | | 100 | 100 | | | 100 | | | 100 | |
| | 1 | 20 | | 98 | 98 | | | 100 | | | 100 | |

TABLE (IX)

| Compound No. | Dose kg/ha | CROPS IN PRE-EMERGENCE TREATMENT ||||||||| 
|---|---|---|---|---|---|---|---|---|---|---|
| | | WHE | MAI | BAR | RIC | RAP | COT | BEA | SOY | SUN |
| 51 | 8 | | | | | | | 0 | | |
|  | 2 | 0 | 5 | 0 | 0 | | 0 | 0 | 50 | 0 |
| 52 | 8 | | | | | | | 0 | | |
|  | 1 | 20 | 0 | 15 | 0 | | 0 | 0 | 0 | 0 |
| 53 | 8 | | | | | | | 0 | | |
|  | 1 | 0 | 0 | 0 | 15 | 10 | 0 | 0 | 0 | 0 |
| 54 | 8 | | | | | | | 30 | | |
|  | 0.5 | 0 | 0 | 0 | 5 | | 0 | 0 | 0 | 0 |
| 55 | 0.5 | 0 | 0 | 0 | 10 | | 0 | 30 | 10 | 0 |
| 56 | 8 | | | | | | | 30 | | |
| 57 | 0.5 | 0 | 0 | 0 | 0 | | 0 | 0 | 0 | 0 |
| 58 | 2 | 0 | 10 | 0 | 30 | | 0 | | 0 | 0 |
| 59 | 2 | 5 | 10 | 0 | 0 | | 0 | 0 | 5 | 0 |
| 60 | 0.5 | 0 | 20 | 0 | 0 | | 0 | 30 | 0 | 0 |
| 61 | 8 | | | | | | | 70 | | |
| 62 | 0.5 | 0 | 0 | 0 | 10 | 20 | 0 | 0 | 10 | 0 |
| 63 | 8 | | | | | | | | | |
| 64 | 8 | | | | | | | | | |
|  | 2 | | | | | | | | | |
| 65 | 8 | | | | | | | | | |
|  | 2 | | | | | | | | | |
| 66 | 1 | 0 | 0 | 0 | 10 | 0 | 0 | 0 | 50 | 0 |
| 67 | 1 | 0 | 0 | 0 | 5 | | 0 | 0 | 0 | 0 |
| 68 | 1 | | | | | | | 30 | | |
| 69 | 2 | 0 | 0 | 0 | 10 | | 0 | 0 | 0 | 0 |
| 70 | 1 | 0 | 60 | 20 | 10 | | 0 | 0 | 0 | 0 |
| 71 | 8 | | | | | | | 30 | | |
| 72 | 1 | | | | | | | 30 | | |
| 73 | 1 | | | | | | | 30 | | |
| 74 | 8 | | | | | | | 0 | | |
| 75 | 2 | 0 | 20 | 10 | 0 | | 0 | 50 | 20 | 0 |
| 76 | 1 | 5 | 20 | 0 | 20 | | 0 | 0 | 0 | 0 |
| 77 | 8 | | | | | | | 0 | | |

TABLE (X)

| Compound No. | Dose kg/ha | ADVENTITIOUS PLANTS or CROPS (Post-emergence treatment) |||||| 
|---|---|---|---|---|---|---|---|
| | | WO | PAN | RAY | GOO | WM | BEA |
| 1 | 8 | 100 | 100 | 100 | 60 | 50 | 0 |
| 2 | 8 | 80 | 90 | 50 | 30 | 60 | |
| 4 | 8 | 30 | 90 | 30 | 20 | 40 | |
| 5 | 8 | 10 | 90 | 60 | 0 | 30 | |
| 6 | 8 | 20 | 95 | 80 | 0 | 30 | |
| 7 | 8 | 30 | 80 | 80 | 0 | 20 | 0 |
| 8 | 8 | 30 | 30 | 30 | 0 | 20 | |
| 10 | 8 | 50 | 100 | 80 | 0 | 0 | |
| 12 | 8 | 30 | 80 | 0 | 30 | 20 | 0 |
| 13 | 8 | 20 | 20 | 60 | 0 | 10 | 0 |
| 14 | 8 | 100 | 100 | 100 | 30 | 70 | |
| 15 | 8 | 70 | 100 | 90 | 20 | 90 | |
| 16 | 8 | 0 | 40 | 0 | 20 | 0 | 0 |
| 17 | 8 | 0 | 40 | 20 | 20 | 0 | 0 |
| 18 | 8 | 20 | 60 | 30 | 20 | 0 | 0 |
| 21 | 8 | 100 | 100 | 100 | 30 | 50 | |
| 22 | 8 | 98 | 100 | 100 | 80 | 100 | |
| 23 | 8 | 30 | 20 | 20 | 30 | 20 | 0 |
| 24 | 8 | 95 | 100 | 80 | 30 | 50 | 0 |
| 25 | 8 | 20 | 60 | 30 | 20 | 20 | |
| 26 | 8 | 30 | 100 | 30 | 20 | 30 | 0 |
| 27 | 8 | 0 | 95 | 70 | 20 | 20 | 0 |
| 28 | 8 | 20 | 100 | 20 | 30 | 80 | 0 |
| 29 | 8 | 0 | 90 | 20 | 20 | 30 | |
| 30 | 8 | 0 | 0 | 0 | 20 | 0 | 0 |
| 31 | 8 | 100 | 95 | 95 | 30 | 30 | |

TABLE (XI)

| Compound No. | Dose kg/ha | ADVENTITIOUS PLANTS or CROPS IN POST-EMERGENCE TREATMENT |||||
|---|---|---|---|---|---|---|
| | | WO | PAN | RAY | WM | GOO |
| 51 | 8 | 20 | 30 | 40 | 0 | 0 |
| 52 | 8 | 40 | 95 | 90 | 0 | 0 |
| 53 | 8 | 70 | 100 | 90 | 30 | 20 |
| 54 | 8 | 60 | 100 | 80 | 90 | 30 |
| 55 | 8 | 30 | 100 | 20 | 20 | 20 |
| 56 | 8 | 0 | 70 | 20 | 0 | 0 |
| 57 | 8 | 100 | 100 | 98 | 30 | 30 |
| 58 | 8 | 50 | 100 | 90 | 80 | 30 |
| 59 | 8 | 70 | 100 | 40 | 30 | 30 |
| 60 | 8 | 98 | 100 | 100 | 90 | 80 |
| 61 | 8 | 20 | 100 | 30 | 90 | 20 |
| 62 | 8 | 20 | 98 | 50 | 70 | 30 |
| 63 | 8 | 10 | 100 | 30 | 100 | 80 |
| 64 | 8 | 0 | 98 | 95 | 30 | 20 |
| 65 | 8 | 95 | 100 | 100 | 70 | 100 |
|  | 2 | 50 | 100 | 95 | 20 | 70 |
| 66 | 8 | 0 | 50 | 20 | 0 | 40 |
| 67 | 8 | 0 | 50 | 30 | 0 | 20 |
| 68 | 8 | 30 | 80 | 20 | 40 | 20 |
| 69 | 8 | 0 | 100 | 50 | 30 | 30 |
| 70 | 8 | 98 | 100 | 100 | 60 | 80 |
| 72 | 8 | 10 | 95 | 80 | 30 | 5 |
| 73 | 8 | 0 | 95 | 80 | 60 | 0 |
| 88 | 1 | 30 | 98 | 80 | 20 | 20 |
| 89 | 1 | 30 | 95 | 20 | 20 | 20 |
| 90 | 1 | 30 | 60 | 70 | 0 | 50 |
| 91 | 1 | 30 | 80 | 30 | 30 | 30 |

TABLE (XII)

| Compound No. | Dose kg/ha | Adventitious plants or crops - Post-emergence treatment ||||||||||||||
|---|---|---|---|---|---|---|---|---|---|---|---|---|---|---|---|
| | | WHE | BAR | RIC | RAP | COT | BEA | SOY | SUN | FIN | PAN | RAY | FOX | SF | BN | CHI |
| 10 | 8 | 5 | 15 | 10 | 10 | 0 | 0 | 30 | 0 | 90 | 80 | 60 | 100 | 90 | 100 | 20 |
| 14 | 2 | 0 | 20 | 0 | 0 | 20 | 0 | 5 | 5 | 60 | 0 | 0 | 20 | 60 | 10 | 100 |
| 15 | 4 | 0 | | | 20 | 0 | 0 | 5 | 0 | 60 | 80 | 0 | 80 | 10 | 90 | 0 |
| 21 | 1 | 10 | 10 | 10 | 0 | 20 | 0 | 0 | 5 | 20 | 80 | 20 | 60 | 95 | 80 | 100 |

TABLE (XII)-continued

| Compound No. | Dose kg/ha | Adventitious plants or crops - Post-emergence treatment | | | | | | | | | | | | | | |
|---|---|---|---|---|---|---|---|---|---|---|---|---|---|---|---|---|
| | | WHE | BAR | RIC | RAP | COT | BEA | SOY | SUN | FIN | PAN | RAY | FOX | SF | BN | CHI |
| 22 | 1 | 0 | 5 | 5 | 0 | 0 | 0 | 10 | 20 | 95 | 95 | 20 | 100 | 70 | 80 | 0 |
| 53 | 4 | 0 | 0 | 0 | 20 | 0 | 0 | 0 | 10 | 80 | 90 | 10 | 85 | 60 | 95 | 10 |
| 54 | 4 | 0 | 5 | 5 | 20 | 0 | 0 | 20 | 0 | 80 | 60 | 0 | 80 | 10 | 30 | 10 |
| 60 | 1 | 0 | 20 | 5 | 0 | 0 | 0 | 0 | 5 | 100 | 90 | 10 | 95 | 0 | 90 | 0 |
| 61 | 4 | 0 | 0 | 0 | 0 | 0 | 0 | 0 | 0 | 20 | 30 | 10 | 90 | 10 | 5 | 0 |
| 63 | 4 | 0 | 0 | 0 | 0 | 20 | 0 | 5 | 0 | 0 | 60 | 0 | 20 | 0 | 90 | 60 |
| 65 | 2 | 0 | 0 | 0 | 10 | 0 | 0 | 0 | 5 | 20 | 80 | 10 | 100 | 10 | 100 | 40 |
| 70 | 1 | 0 | 20 | 10 | 0 | 0 | 0 | 0 | 0 | 50 | 80 | 5 | 10 | 80 | 10 | 80 |

We claim:

1. A compound of the formula:

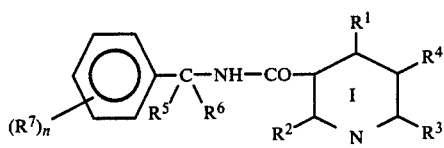

wherein:
R$^1$, R$^2$ and R$^3$, which are identical or different, represent the hydrogen atom, a lower alkyl radical, a lower alkoxy radical or an alkoxyalkyl radical having from 2 to 8 carbon atoms:

R$^4$ represents a carboxyl radical or salt thereof or the radical —COOR$^8$, wherein R$^8$ represents a lower alkyl radical, or the cyano radical, a lower cyanoalkyl radical or an alkoxyalkyl radical having from 2 to 8 carbon atoms;

R$^5$ and R$^6$ represent the hydrogen atom or a lower alkyl radical or together form a single divalent alkylene radical having from 2 to 5 carbon atoms or one of radicals R$^5$ and R$^6$ represent a cyano radical;

R$^7$ represents a halogen atom, a lower alkyl radical, a lower alkoxy radical, a lower alkenyl radical, a lower alkenyloxy radical wherein the lower alkyl radical, alkoxy radical, alkenyl radical and lower alkenyloxy radical is optionally halogen-substituted, a nitro or cyano radical or an amino radical which is optionally substituted by one or two identical or different lower alkyl radicals or by a radical —CO—R$^9$, wherein R$^9$ represents a lower alkyl radical, lower alkoxy radical, lower alkylamino radical or dialkylamino radical, wherein each of the lower alkyl radicals, lower alkoxy radicals, lower alkylamino radicals or dialkylamino radicals are identical or different and contain at most 6 carbon atoms; or, when n is greater than 1, two of R$^7$ may together represent an alkylenedioxy group having from 1 to 4 carbon atoms;

n is zero or a positive interger equal to at most 5; and the heterocyclic ring

represents the dihydropyridine nucleus

2. A compound according to claim 1 in which R$^4$ represents a radical —COOR$^8$, wherein R$^8$ comprises a lower alkyl radical, or R$^4$ represents a lower alkoxyalkyl radical or a lower cyanoalkyl radical.

3. A compound according to claim 1 wherein:
R$^1$ is the hydrogen atom;
R$^2$ and R$^3$ are the methyl, methoxy or methoxymethyl radical;
R$^4$ is COOR$^8$ comprises from 1 to 4 carbon atoms, or R$^4$ is a cyanomethyl or lower alkoxymethyl radical;
R$^5$ and R$^6$ are the hydrogen atom or one of R$^5$ or R$^6$ is the methyl radical, or R$^5$ and R$^6$ together form an ethylene chain;
R$^7$ is a chlorine atom, fluorine atom, an alkyl radical having from 1 to 4 carbon atoms, which is optionally halogen-substituted, or an alkoxy radical having from 1 to 4 carbon atoms; and
n is equal to 0, 1 or 2.

4. A compound according to claim 1, which is in the form of an optical isomer having the same configuration as

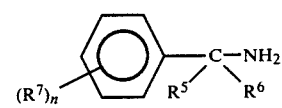

5. A herbicidal composition which contains, as the active ingredient, a herbicidally effective amount of at least one compound according to calim 1, in an inert agriculturally acceptable carrier.

6. A composition according to claim 5, which contains 0.05 to 95% by weight of active ingredient.

7. A composition according to claim 6, which also contains 1 to 94.95% of a solid or liquid carrier and, if appropriate, 0.1 to 20% of one or more surface-active agents.

8. A process for selectively destroying weeds in cotton, sunflower, wheat or barley, which comprises applying, to the plants and/or to the soil in the zone in which weeds are to be destroyed, an effective amount of at least one compound according to claim 1.

9. A process according to claim 8, wherein between 0.1 and 10 kg/ha of the active ingredient is applied.

10. A process according to claim 8, wherein the application is carried out as a pre-emergence treatment of the crops or as a pre-sowing treatment of the crops with incorporation.

* * * * *